United States Patent [19]

Simpson

[11] 4,447,155

[45] May 8, 1984

[54] DETECTION OF LIGHT-AFFECTING SUBSTANCE IN A FLUID

[75] Inventor: Colin A. Simpson, Iver, England

[73] Assignee: Graviner Limited, England

[21] Appl. No.: 245,565

[22] Filed: Mar. 19, 1981

[30] Foreign Application Priority Data

Mar. 29, 1980 [GB] United Kingdom ............ 8010686

[51] Int. Cl.³ ................ G01N 1/26; G01N 21/11
[52] U.S. Cl. ......................... 356/437; 356/439; 356/440
[58] Field of Search ............ 356/246, 437, 438, 439, 356/440; 250/576

[56] References Cited

U.S. PATENT DOCUMENTS 3,207,026 9/1965 Churchill et al. .............. 356/440
4,290,698 9/1981 Milana ........................... 356/448

FOREIGN PATENT DOCUMENTS 707699 4/1952 United Kingdom.
1352004 7/1971 United Kingdom.

*Primary Examiner*—Vincent P. McGraw
*Attorney, Agent, or Firm*—John K. Williamson

[57] ABSTRACT

Apparatus for detecting oil mist or other light-affecting contamination in a fluid comprises a measuring chamber across which a light source directs a beam of light on to a photocell. Solenoid valves each control the connection of a respective inlet pipe (connected, for example, to a particular part of an internal combustion engine being monitored for oil mist) to the measuring chamber. The solenoid valves are operated in sequence so as to admit respective samples of the atmosphere into the measuring chamber where the degree of contamination is detected by the changing photocell output. The samples are drawn into the measuring chamber by suction from a fan unit. The fan unit is also connected by a by-pass chamber and by-pass pipes in the individual valve units to the inlet pipes on the upstream sides of the valves. In this way, the inlet pipes are kept charged with atmosphere from the areas being monitored so that each sample is very rapidly sucked into the measuring chamber when a valve is opened.

5 Claims, 3 Drawing Figures

DETECTION OF LIGHT-AFFECTING SUBSTANCE IN A FLUID

BACKGROUND OF THE INVENTION

The invention relates to apparatus responsive to a light-affecting substance in a fluid such as, for example, oil mist in an atmosphere. An embodiment of the inventon to be described is a detector for detecting lubricating oil mist of excessive concentration occurring during the running of rotating plant and machinery and especially for detecting such mists in the crank cases of internal combustion engines including diesel engines. Excessive oil mist formation may constitute an explosion hazard and it is clearly advantageous to be able to detect, at an early stage, such excessive oil mist formations. Excessive oil mist formation in crankcases may occur as a result of overheating or wear of mechanical parts, and means for detecting such excessive oil mist formations also enables early remedial action to be taken to prevent further damage.

However, the invention is also applicable to the detection of other light affecting substances and to the detection of mist in general, for example, the detection of vapour mists in air conditioning, refrigerating and gas cooling systems. Detection of colourless mists is possible by, for example, passing the mist over an appropriate chemical which will react to colour the mist. Furthermore, the densities of exhaust gases from internal combustion engines can be measured.

Arrangements are known in which samples of fluids are taken sequentially using a mechanical rotary valve, and the presence of light-affecting substances in each sample then detected photo-electrically. Such arrangements are slow and cumbersome.

An object of the invention is to provide improved apparatus responsive to light-affecting substances in a fluid.

A more specific object is to provide such apparatus capable of operating at high speed so as to enable a number of samples to be taken and measured individually within a very short total cycle time.

BRIEF SUMMARY OF THE INVENTION

According to the invention, there is provided apparatus for detecting a light-affecting substance in a fluid, comprising a plurality of solenoid-operated valves each having a respective inlet pipe, a respective outlet pipe, a respective bypass pipe, a respective solenoid coil, and a respective valve member which is movable by the solenoid coil between a closed position in which it blocks communication between the valve inlet pipe and the valve outlet pipe but connects the valve inlet pipe to the bypass pipe and an open position in which it connects the valve inlet pipe to the valve outlet pipe and blocks communication between the valve inlet pipe and the bypass pipe; a common measuring chamber to which all the valve outlet pipes are connected; means applying suction to the measuring chamber and to all the bypass pipes whereby the suction applied by the bypass pipes to the valve inlet pipes of all the valves whose valve members are in the closed position draws fluid into, so as to fill, each such valve inlet pipe, and the suction applied via the measuring chamber to the valve inlet pipe of each valve whose member is in the open position draws a sample of fluid from that valve inlet pipe into the measuring chamber; the photo-electric detecting means in the measuring chamber for photo-electrically detecting a light-affecting substance in each fluid sample.

Oil mist detection apparatus embodying the invention will now be described, by way of example only, with reference to the accompanying diagrammatic drawings in which.

DESCRIPTION OF PREFERRED EMBODIMENTS

Figure 1:
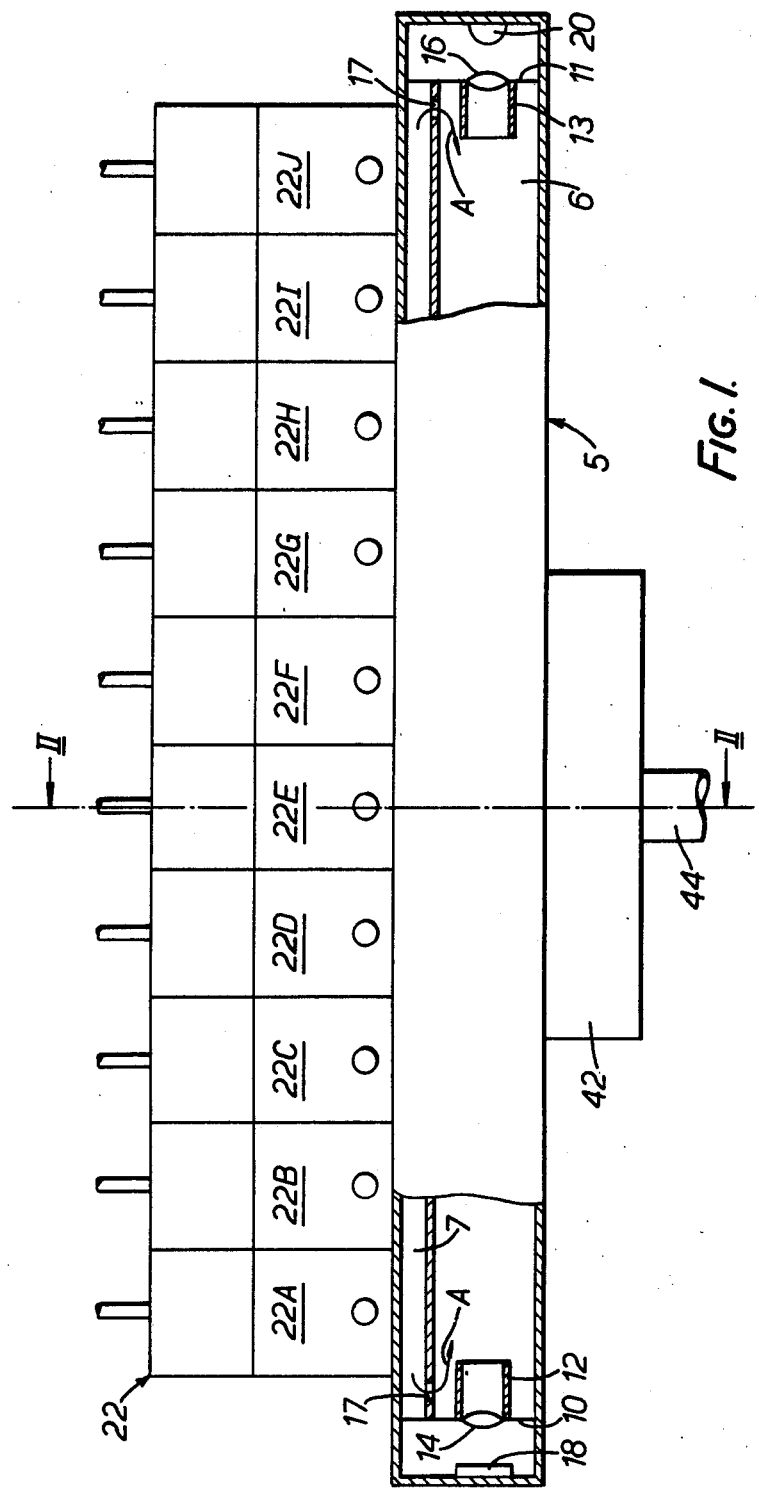
FIG. 1 is a side view of the apparatus, partly broken away to show internal construction.
Figure 2:
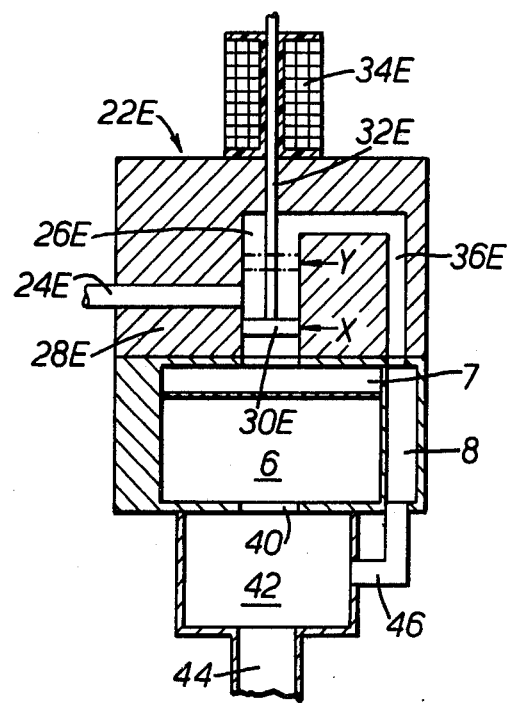
FIG. 2 is a section on the line II—II of FIG. 1.

As shown in FIG. 1, the apparatus comprises a housing 5 which contains three chambers, a measuring chamber 6, a diffusing chamber 7 and a bypass chamber 8 (see FIG. 2). These chambers each extend between two end walls 10 and 11 which are shown in FIG. 1 where part of the outside of the housing 5 is broken away. Each end wall 10, 11 incorporates a window from which inwardly extends a respective open-ended cylindrical extension 12, 13. Mounted in each window is a respective lens 14, 16. The lenses 14, 16 open into opposite ends of the measuring chamber 6 but do not open into the bypass chamber 8.

The diffusing chamber 7 opens into the measuring chamber 6 through two ports 17.

Between the dividing wall 10 and the end of the housing 5 is a space in which a photo-electric cell is mounted in alignment with the lens 14. At the opposite end of the housing 5, and between the end wall of the housing and the dividing wall 16, is mounted an electrically energisable lamp 20 in alignment with the lens 16.

A valve assembly 22 is mounted on the housing 5. The valve assembly 22 consists of ten (in this example) solenoid-operated valves 22A to 22J. The valve 22E is illustrated in detail in FIG. 2.

As shown, the valve 22E has an inlet 24E which open into a valve chamber 26E in a valve housing 28E. A piston or valve member 30E is mounted within the vale chamber 26E and slidable between the position shown at X and the position shown at Y. The piston 30E is connected to a valve operating rod 32E which can be electromagnetically raised and lowered by a solenoid coil 34E, so as to move the piston between the positions X and Y.

The valve chamber 26E opens into the diffusing chamber 7. At its opposite end it is connected by a pipe 36E to the bypass chamber 8.

All the other solenoid valves are constructed similarly to the solenoid valve 22E shown in FIG. 2.

FIG. 2 also shows how the measuring chamber 6 is connected through a relatively large opening 40 to a fan unit 42 and an exhaust port 44. The bypass chamber 8 is also connected to the fan unit 42 and the exhaust 44 by a pipe 46.

Suction is applied to the measuring chamber 6 and the bypass chamber 8, via the opening 40 and the pipe 46 respectively, by means of a fan (not shown) incorporated in the fan unit 42.

In operation, the inlet pipes 24 of all the solenoid valves are connected to different parts of the internal combustion engine being monitored. In other applications, they could for example be connected to different parts of an area being monitored for contamination or to different interna combustion engines.

When all the solenoid valves are in the closed position shown in FIG. 2, that is, with their pistons 30 in the position X, atmosphere is drawn in through the inlet pipe 24 in each valve by the suction applied from the fan unit 42 through the bypass chamber 8. By this means, therefore, each inlet pipe 24, each valve chamber 26 and each pipe 36 is fully charged with the atmosphere from the area being monitored.

The solenoid valves are then opened in sequence, that is, each solenoid is momentarily electrically energised so as to lift its piston 30 momentarily to the position Y, the piston then being lowered to the position X to close the valve before the next valve in the sequence is opened. As each valve is opened, it connects its inlet pipe 24 to the measuring chamber 6 via the diffusing chamber 7 and the ports 17 and a sample of the atmosphere is thus drawn through the diffusing chamber 7 and then through the measuring chamber 6 by the suction from the fan unit 42, the direction of flow being shown by the arrows A in FIG. 1. As the sample passes through the measuring chamber, it passes across the light beam from the lamp 20 to the photocell 18. If the sample contains oil mist (or other light-affecting substances to be monitored), the amount of light falling on the photocell 18 will be reduced and there will be a consequent alteration in the photocell output. This can be recorded and/or indicated, and a warning output given if the change in photocell output indicates a dangerous level of contamination.

The solenoid valves can of course be opened in any sequence and not necessarily in the sequence 22A, 22B, 22C... 22J. It is also possible to open all (or some only) of the solenoid valves together so as to measure the average contamination present in a combination of areas. An an extension of this, the valves may be operated in a sequence which is such that the level of contamination (if any) in each sample is compared with the average level of contamination present in all (or some) of the samples.

The cylindrical extensions 12, 13 help to prevent contamination from falling on the lenses 14, 16.

Figure 3:
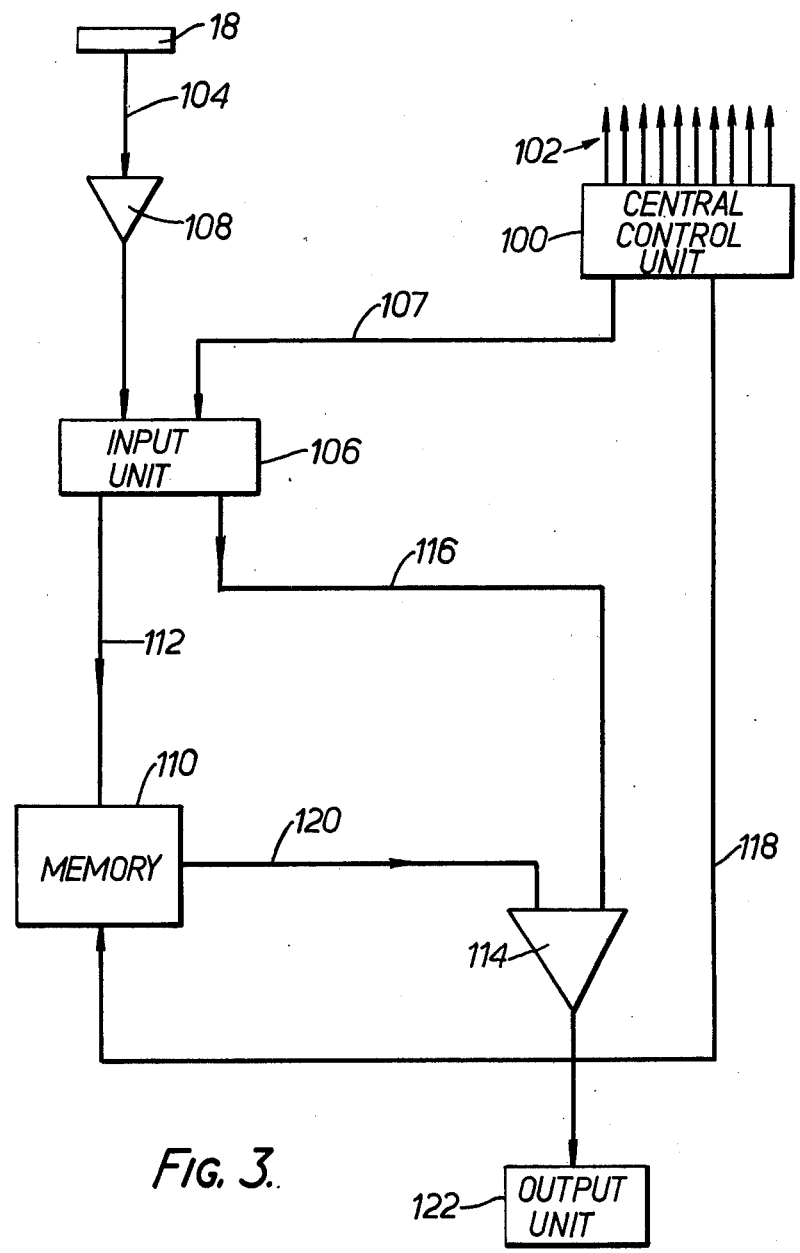
FIG. 3 is a block diagram of the electrical circuit of the apparatus.

FIG. 3 shows the circuitry of the apparatus in block diagram form.

As shown, the circuitry includes a central control unit 100 which has ten output lines 102 respectively connected to the solenoid valves 22A to 22J for opening them according to a predetermined sequence. The electrical output from the photocell 18 is developed on a line 104 and fed to an input unit 106 via an amplifier 108. The input unit 106 is controlled via a line 107 by the central control unit 100 and can transmit the output of amplifier 108 either to a memory 110, by means of a line 112, or to a compartor 114 by means of a line 116.

By means of a line 118, the central control unit 100 can read the memory 110 and feeds the stored signal to the second input of the comparator 114 on a line 120.

If the apparatus is operating in the mode in which it compares the level of contamination in the sample admitted by each solenoid valve with the average of all the samples, then the central processing unit 100 will first energise all the lines 102 so as to open all the solenoid valves. The photocell 18 will therefore produce an electrical output dependent on the average level of contamination, and the unit 100 will energize line 107 so as to cause the input unit 106 to direct this electrical signal to the store 110.

The central control unit 100 will then close all the solenoid valves and then open them sequentially, one by one. As each valve is opened, the unit 100 energises line 107 so as to cause the input unit 106 to direct the resultant electrical signal from the photocell 18 to the comparator 114. At the same time, the unit 100 energises line 118 to read out the previously stored average level signal from the memory 110 and to feed this to the second input of the comparator 114. If the comparator indicates that the level of contamination exceeds a predetermined amount based on the average level of contamination, it produces a warning output to a display or other output unit 122.

In another mode, the system can be arranged such that one of the solenoid valves has its input 24 connected not to an area whose contamination is to be monitored but to a source of clean, uncontaminated, air. The other solenoid valves can be subsequently opened, in sequence, and the level of contamination (if any) sensed by the photocell 18 in response to the sample admitted by each opened valve can be compared with the previously stored "no-contamination" level. A warning signal is then given if the level of contamination in any particular sample exceeds a predetermined level based on the "no-contamination" level.

In this mode, the unit 100 will first energise the appropriate one of the lines 102 so as to open the solenoid valve receiving the clean atmosphere and by means of line 107, the unit 100 will direct the resultant electrical signal into the memory 110. Subsequently the unit 100 closes that solenoid valve and opens the others sequentially, one by one. In the manner described above, the unit 100 will then cause the comparator to compare each resultant photocell output with the stored signal to produce a warning output when the contamination exceeds the predetermined level.

If the apparatus is operating in neither of those modes but is arranged simply to compare the level of each photocell output with a fixed level, then the memory 110 would be replaced by means for setting up a signal representing this fixed level (e.g. an adjustable potential divider), and this signal would be fed into the second input of the comparator 114 for comparison with each photocell output as the solenoid valves are opened in turn.

The apparatus described is advantageous because the solenoid valves can be made very fast-acting, much faster acting than can other types of purely mechanical valve such as rotary valves or the like in which a common outlet pipe is provided which is successively swung into communication with the individual inlet pipes. The apparatus is able to make best use of the fast acting nature of the solenoid valves because of its use of the bypass chamber and the arrangement of the valves such that each valve and its associated inlet pipe are maintained fully charged with the atmosphere being sampled, even when the valve is not open. This means that the sample of atmosphere is almost instantaneously diverted into the measuring chamber 6 when the valve is opened and substantially instaneaneous measurement can take place. If, for example, no bypass chamber 8 were provided, and each valve piston 30 was merely arranged to open and close the connection between the inlet 24 and the measuring chamber 26, then there would be a time delay (after opening of the valve) before the suction in the fan unit 42 would be able to draw a sample of the atmosphere into the inlet pipe 24 and the measuring chamber 6 from the area being monitored. The arrangement described ensures that all the inlet pipes are continuously filled with the atmosphere from the areas being monitored.

What is claimed is:

1. Apparatus for detecting a light-affecting substance in a fluid, comprising
   a housing,
   a plurality of solenoid-operated valves mounted side-by-side in the housing and each having a respective inlet pipe, a respective outlet pipe, a respective bypass pipe, a respective solenoid coil, and a respective valve member which is movable by the solenoid coil between a closed position in which it blocks communication between the valve inlet pipe and the valve outlet pipe but connects the valve inlet pipe to the bypass pipe and an open position in which it connects the valve outlet pipe to the valve inlet pipe and blocks communication between the valve inlet pipe and the bypass pipe;
   a common diffusing chamber defined in the housing immediately adjacent to the solenoid-operated valves and to which the valve outlet pipes are immediately connected;
   a common measuring chamber defined by the housing immediately adjacent to the diffusing chamber and to which the diffusing chamber is immediately connected;
   a bypass chamber defined by the housing and to which all the bypass pipes are connected;
   a fan unit supported by the housing and in common communication with the measuring and bypass chambers to apply suction to the valves and to all the bypass pipes whereby the suction applied by the bypass pipes via the bypass chamber to the valve inlet pipes of all the valves whose valve members are in the closed position draws fluid into, so as to fill, each such valve inlet pipe, and the suction applied via the measuring chamber and the diffusing chamber to the valve inlet pipe of each valve whose valve member is in the open position draws a sample of fluid from that valve inlet pipe through the diffusing chamber into the measuring chamber;
   photo-electric detectig means in the measuring chamber for photo-electrically detecting a light-affecting substance in each fluid sample; and
   control means for energizing the solenoid coil in a predetermined sequence.

2. Apparatus according to claim 1, in which the photo-electrical detecting means comprises a source of light for directing a light beam through the measuring chamber to a photo-electric cell.

3. Apparatus according to claim 1, including storage means arranged to store an electrical signal representing a predetermined datum value of contamination in the fluid, control means operative to activate the said valves in a predetermined sequence whereby each valve member moves temporarily into the open position, and comparing means operative to compare the electrical output produced by the photo-electric detecting means in response to activation of each valve in turn with the stored electrical signal, whereby to indicate whether the level of contamination in the respective sample of fluid drawn in through that valve is above or below the datum value of contamination.

4. Apparatus according to claim 3, in which the control means is operative to activate all the valves simultaneously whereby all the valve members move simultaneously into their open positions so that the photo-electric detecting means produces an electrical output representing the average level of contamination in all the samples of fluid drawn through the valves, and means feeding this electrical output into the storage means to represent the predetermined datum value of contamination.

5. Apparatus according to claim 3, in which the inlet pipe of one said valve is connected to substantially uncontaminated fluid whereby the electrical output produced by the photo-electric detecting means when that valve is activated in the said sequence represents substantially uncontaminated fluid, and including means feeding this electrical output into the storage means to represent the predetermined datum value of contamination.

* * * * *